(12) United States Patent
Legerton et al.

(10) Patent No.: US 11,953,761 B2
(45) Date of Patent: *Apr. 9, 2024

(54) GEOMETRIC VOLUME CONTROL CORNEAL REFRACTIVE THERAPY CONTACT LENS

(71) Applicant: SHENYANG KANGENDE MEDICAL SCIENCE AND TECHNOLOGY CO., LTD., Shenyang (CN)

(72) Inventors: Jerome A. Legerton, Jupiter Inlet Colony, FL (US); Jidong Liu, Shanghai (CN); Gaozhi Liu, Shenyang (CN)

(73) Assignee: Shenyang Kangende Medical Science and Technology Co., Ltd., Shenyang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,037

(22) Filed: Feb. 15, 2023

(65) Prior Publication Data

US 2023/0221581 A1 Jul. 13, 2023

Related U.S. Application Data

(63) Continuation of application No. 17/616,154, filed as application No. PCT/CN2021/078909 on Mar. 3, 2021, now Pat. No. 11,774,779.

(51) Int. Cl.
*G02C 7/04* (2006.01)
*A61F 9/013* (2006.01)

(52) U.S. Cl.
CPC .............. *G02C 7/047* (2013.01); *A61F 9/013* (2013.01)

(58) Field of Classification Search
CPC ................................ G02C 7/047; A61F 9/013
(Continued)

(56) References Cited

U.S. PATENT DOCUMENTS 5,880,809 A 3/1999 Lieberman et al.
11,454,825 B2 9/2022 Fabre
(Continued)

FOREIGN PATENT DOCUMENTS

CN 1672084 A 9/2005
CN 1672085 A 9/2005
(Continued)

OTHER PUBLICATIONS

International Search Report and Written Opinion for Application No. PCT/CN2021/078909, dated Sep. 28, 2021.
(Continued)

*Primary Examiner* — James R Greece
(74) *Attorney, Agent, or Firm* — Sheppard Mullin Richter & Hampton LLP

(57) ABSTRACT

A contact lens for treating myopia of an eye of a patient comprises an anterior surface; and a posterior surface having a semi-meridian defining: a central compression zone to contact the pretreatment cornea, a volume control zone peripheral to the central compression zone, a secondary compression zone to contact the pretreatment cornea, wherein the secondary compression zone is peripheral to the volume control zone, a peripheral relief zone peripheral to the secondary compression zone, a landing zone to contact the pretreatment cornea, wherein the landing zone is peripheral to the peripheral relief zone, and an edge terminus peripheral to the landing zone.

24 Claims, 6 Drawing Sheets

(58) Field of Classification Search
USPC .................................................. 351/159.23
See application file for complete search history.

(56) References Cited

U.S. PATENT DOCUMENTS

| | | | |
|---|---|---|---|
| 2006/0152673 A1 | 7/2006 | Cotie et al. | |
| 2009/0040458 A1 | 2/2009 | Ye et al. | |
| 2009/0237612 A1 | 9/2009 | Cotie et al. | |
| 2016/0299356 A1 | 10/2016 | Mitsui | |
| 2021/0031471 A1* | 2/2021 | Newman | B29D 11/00076 |

FOREIGN PATENT DOCUMENTS

| | | | | |
|---|---|---|---|---|
| CN | 101002132 A | | 7/2007 | |
| CN | 101523270 A | | 9/2009 | |
| CN | 104823100 A | | 8/2015 | |
| CN | 106461970 A | | 2/2017 | |
| CN | 110235051 A | * | 9/2019 | ............. G02B 1/043 |
| CN | 110235051 A | | 9/2019 | |
| CN | 111033360 A | | 4/2020 | |
| CN | 212364749 U | | 1/2021 | |
| WO | 2004/011991 A1 | | 2/2004 | |
| WO | 2006/014681 A1 | | 2/2006 | |
| WO | 2017/149512 A1 | | 9/2017 | |
| WO | 2018/112558 A1 | | 6/2018 | |
| WO | 2018/234666 A1 | | 12/2018 | |

OTHER PUBLICATIONS

First Search dated May 12, 2022, issued in related Chinese Application No. 202180003258.5 (2 pages).
First Office Action dated May 17, 2022, issued in related Chinese Application No. 202180003258.5, with English machine translation (9 pages).
Extended European Search Report dated Feb. 13, 2024, issued in related European Patent Application No. 21928498.1 (8 pages).

* cited by examiner

GEOMETRIC VOLUME CONTROL CORNEAL REFRACTIVE THERAPY CONTACT LENS

This application is a continuation of U.S. application Ser. No. 17/616,154, filed on Dec. 2, 2021, now allowed, which is a 371 National Stage Entry of PCT Application No. PCT/CN2021/078909, filed on Mar. 3, 2021.

DESCRIPTION OF RELATED ART

The disclosed technology relates generally to contact lenses, and more particularly some embodiments relate to contact lenses and non-surgical methods for reshaping the cornea of an eye to treat visual acuity deficiencies.

BACKGROUND

Rigid contact lenses were commercialized more than 60 years ago. Initial fitting concepts quickly evolved to bi-curve and tri-curve designs to facilitate the required lens movement for tear exchange in lenses that were not gas permeable. Lens movement with the blink was imperative to allow a fresh tear layer to move from the tear meniscus at the lower lid to beneath the lens. The simple lathes used in the first two decades of commercialization allowed for concentric curves which were blended to avoid sharp junctions.

The central radius of the lens was selected in relationship to the central corneal curvature. The base curve radius could be equal to, greater than, or shorter than the central corneal curvature based on the philosophy of the design. The radius of the first concentric zone (secondary curve) was always greater than the base curve radius and the radius of each consecutive zone peripheral to the more medial zone was also respectively greater than the zone just medial to it. Lenses historically had three or more zones. All zones outside the central optic zone where, as a rule, greater in radius than the underlying corneal radius. This was a requirement to facilitate lens movement and tear exchange.

Lenses of these designs demonstrated movement with the blink and with lateral eye movement as great as 1.0 to 1.5 mm. Adaptation was required to become accustomed to the movement. Edge design was also very important to achieve comfort and prevent trauma to the bulbar and palpebral conjunctiva.

The advent of gas permeable materials reduced the need for the high degree of movement and the radial and axial edge lift that was required in non-gas permeable lenses. Even so, the traditional design concepts were perpetuated and used with the new materials. Over time, the lenses were designed to have less clearance. In the original designs it was common to have a secondary curve radius that was of the order of 1.4 mm greater than the base curve radius, while in the gas permeable designs they trended toward 0.8 mm greater than the base curve radius. The mean difference of the base curve radius from the central corneal radius also trended in the shorter direction.

In the last decade the mean overall diameter has also trended in the larger direction. As a result, the modal modern gas permeable lens is larger and more closely aligned with the cornea. Early non-gas permeable lenses made of polymethylmethacrylate (PMMA) were designed to have axial edge lift approaching 100 microns while modern lenses may have as little as 50 microns of axial edge lift. Modern gas permeable lenses also demonstrate movement of the order of 0.25 mm or less as compared to 1.0 to 1.5 mm in early PMMA lenses.

Even so, the contemporary design concepts and teaching continue to use concentric zone features and their respective modulation. Lenses and design programs refer to each zone width and local radius. Education curricula teach the modulation in terms of making the radii "flatter" or "steeper" and "narrower" or "wider". Since there exists no commonly available precise metrology for measuring the actual clearances of lenses and since the determination of the fit is by way of sodium fluorescein observations, the assessment of the fit is a learned art rather than a measurement-based science.

At the same time market dynamics demand efficient time management in the fitting of contact lenses. Chair time must be reduced, and first-time success rates are an important metric for productivity and optimized channel economics. Lens fitting concepts must be simple and must demand less training for a successful outcome.

The rigid gas permeable lens designs for overnight corneal reshaping have progressed primarily by way of rational fitting systems where the parameters of pre-determined zones are modulated to control the apical lens radius to the apical corneal radius relationship, the midperipheral lens sagittal depth and midperipheral corneal sagittal depth relationship and the alignment of the periphery of the lens to the peripheral cornea. Those skilled in the art know that the cornea is not rotationally symmetrical and yet all commercialized lens designs are rotationally symmetrical. The result of placing a rotationally symmetrical lens on a rotationally asymmetrical cornea is lens decentration. Random treatment accuracy is also an undesired outcome.

Extensive and persistent efforts have been made to fit these rotationally asymmetric eyes having significant irregular elevation differences with lenses that are rotationally symmetrical. In some cases, toric peripheral designs or dual elevation designs are used to accommodate orthogonal corneal elevation differences. There is a need for non-orthogonal elevation control that is achieved by designing lenses with individual semi-meridian elevation control points. Each semi-meridian of the lens can be designed to have pre-determined elevations at the respective control points defined by their distance from the geometric center of the lens. The elevation or sagittal depth of each point from the geometric center of the back of the lens is determined by the topography of the underlying respective eye at the same location and the design philosophy algorithm describing the desired sagittal depth relationship. These elevation differences are intended to correspond to the irregular elevation of the underlying cornea when the lens is applied to the eye.

Unfortunately, the standard design paradigm of using concentric curves would result in a non-centered lens having its contact with the cornea somewhere near the corneal apex and a random volume of tear fluid under the secondary reverse curve along with a variable contact of the lens to the cornea in the alignment zone in the periphery of the lens. The outcomes with the second generation overnight corneal reshaping lenses include induced higher order aberrations and the inability to accurately and consistently create the mid peripheral power needed for consistent myopia control. While attempts could be made to manage the corneal asymmetry with the second-generation designs, their use of co-axial concentric radii of curvature is inherently self-limiting. The precision and ability to experience consistency in fitting is questionable.

The same limitations are inherent in the third-generation design that incorporates a third order polynomial in the second zone of the lens. The manufacturer of the third-generation design has not commercialized the design in which the third order polynomial is varied by semi-meridian to produce a rotationally asymmetric elevation and the respective regulatory approvals do not include the use of individual semi-meridian elevation control. Furthermore, the third-generation design does not teach controlling the volume between the untreated cornea and the lens in the mid-periphery of the lens, having a controlled inward facing angle for a secondary compression zone of the lens, or having a secondary clearance zone to allow a mid-peripheral corneal contact region to compress into the cornea.

The problem remains that the skill level of the fitter must be high and exhaustive fitting sets or lens re-orders are required to find an optimum fit even when a third-generation lens design addresses the semi-meridian specific sagittal depths.

SUMMARY

Embodiments of the apparatus and method may include one or more of the following features. Some embodiments comprise a posterior surface of a contact lens having a shape determined to geometrically control the area in at least a single semi-meridian of the space between the surface of the contact lens and an underlying corneal surface defined by a first radial location on the posterior surface and a second radial location of the posterior surface and the same radial locations of the corneal surface to be treated. Some embodiments comprise a posterior surface of a contact lens that is has a predetermined inward facing angle from a point of contact of a mid-peripheral portion of the lens with the underlying corneal surface to be treated that forms the peripheral aspect of the geometrically controlled area of the space between the posterior surface of the contact lens and the underlying corneal surface.

In general, one aspect disclosed features a contact lens for reshaping a pretreatment cornea of an eye of a patient, comprising: an anterior surface; and a posterior surface having a semi-meridian defining: a central compression zone to contact the pretreatment cornea, a volume control zone peripheral to the central compression zone, a secondary compression zone to contact the pretreatment cornea, wherein the secondary compression zone is peripheral to the volume control zone, a peripheral relief zone peripheral to the secondary compression zone, a landing zone to contact the pretreatment cornea, wherein the landing zone is peripheral to the peripheral relief zone, and an edge terminus peripheral to the landing zone.

Embodiments of the contact lens may include one or more of the following features. In some embodiments, a radius of the central compression zone is spherical. In some embodiments, a radius of the central compression zone is aspherical. In some embodiments, a diameter of the central compression zone is between 3.0 and 7.0 mm. In some embodiments, the volume control zone is defined by at least four geometric control points connected by one of: a spline, a polynomial, or a combination of conic sections and uncurved segments, a second geometric control point is peripheral to a first geometric control point; a third geometric control point is peripheral to the second geometric control point; and a fourth geometric control point to contact the pretreatment cornea, wherein the fourth geometric control point is peripheral to the third geometric control point. In some embodiments, the first geometric control point of the volume control zone is positioned to have a z-axis separation from the pretreatment cornea in a range of 5 and 80 microns. In some embodiments, the second geometric control point of the volume control zone is positioned to have a z-axis separation from the pretreatment cornea that defines a predetermined area between the posterior surface and the pretreatment cornea in the volume control zone. In some embodiments, the third geometric control point of the volume control zone is positioned to define a predetermined angle between (i) a line connecting the third and fourth control points and (ii) a horizontal line through the fourth control point. In some embodiments, a semi-chord radial distance of the fourth geometric control point is in a range of 2.6 mm to 5.2 mm. In some embodiments, the secondary compression zone has a width in a range of 0.2 mm to 0.8 mm. In some embodiments, the secondary compression zone is defined by a shape having at least one control point within the secondary compression zone, the shape defined by one of: a spline; a polynomial; or a convex conic section. In some embodiments, the peripheral relief zone is defined by at least one control point positioned to have a z-axis separation from the pretreatment cornea that is at least 6 microns per diopter of attempted reduction of central refractive error. In some embodiments, the peripheral relief zone has a width of between 0.4 mm and 1.2 mm. In some embodiments, the peripheral landing zone is defined by a shape having at least one control point within the peripheral landing zone, the shape defined by one of: a spline; a polynomial; a conic section; an angled curved section; or an angled uncurved section. In some embodiments, an edge terminus of the posterior surface commences at the most radially peripheral aspect of the peripheral landing zone and connects to the most peripheral aspect of the anterior surface; and the edge terminus of the posterior surface is defined by: an ellipse, a conic section, or a spline. In some embodiments, the volume control zone and the secondary compression zone are defined by a single spline.

In general, one aspect disclosed features a method for defining a contact lens to be manufactured for an eye of a patient, the method comprising: selecting, according to corneal topography of the eye of the patient: a base curve radius of a central compression zone of the contact lens, a peripheral semi-meridian radial distance of the central compression zone of the contact lens, an area of a volume control zone adjacent to the central compression zone, and a semi-chord radial distance of a secondary compression zone to contact a pretreatment cornea of the eye, wherein the secondary compression zone is adjacent and peripheral to the volume control zone; determining locations of a plurality of control points to define at least the central compression zone width, the shape of the volume control zone to produce a pre-determined area between the surface of the zone and the surface of the cornea to be treated, the semi-meridian radial distance of the secondary compression zone, the inward facing angle formed at the apex of the secondary compression zone; and defining a semi-meridian of a posterior surface of the contact lens according to the plurality of control points.

Embodiments of the method may include one or more of the following features. Some embodiments comprise locating a first one of the control points at the geometric center of the contact lens and the corresponding geometric center of the pretreatment cornea. Some embodiments comprise determining the base curve radius according to manifest refraction and keratometry or topographic measurement of the eye; selecting a semi-chord radial distance of a second one of the control points as a peripheral terminus of the central compression zone; and setting a sagittal depth of the second one of the control points at the sagittal sag of the selected base curve radius at the selected semi-chord radial distance of the second one of the control points while the first one of the control points is in contact with the underlying pretreatment cornea. Some embodiments comprise selecting a semi-chord radial distance of a third one of the control points to separate a first region of the volume control zone and a second region of the volume control zone peripheral to the first region of the volume control zone; and setting a sagittal depth of the third one of the control points at a distance equal to the distance of a lens having a predetermined diopter treatment target radius when placed on a mean pretreatment cornea. Some embodiments comprise selecting a semi-chord radial distance of a fourth one of the control points equal to the semi-chord radial distance of an apex of the secondary compression zone according to a desired mid-peripheral add location. Some embodiments comprise selecting a squeeze angle of a peripheral aspect of the second region of the volume control zone; and locating a fifth one of the control points to define the squeeze angle with the fourth one of the control points. Some embodiments comprise determining a location of a sixth one of the control points according to the selected area of the volume control zone according to the desired mid peripheral add power. Some embodiments comprise determining an overall diameter of the contact lens according to a corneal diameter of the pretreatment cornea; and determining a location of a seventh one of the control points according to the overall diameter of the contact lens. Some embodiments comprise determining an eighth one of the control points to define a medial aspect of a landing zone to contact the pretreatment cornea according to the corneal topography of the eye and the desired radial distance from the seventh one of the control points according to the desired radial width of a landing zone. Some embodiments comprise selecting a diameter of a ninth one of the control points; selecting an area of a peripheral relief zone between the secondary compression zone and the landing zone; and determining a sagittal depth of the ninth one of the control points according to the selected area of the peripheral relief zone or according to the targeted treatment in diopters.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Embodiments of the disclosed technology provide corneal refractive therapy (CRT) contact lenses for overnight corneal reshaping, and methods for defining the CRT contact lenses using geometry volume control techniques. These techniques employ spline mathematics or other geometry to determine the surface contour of a contact lens at predetermined control points or knots on the posterior surface of the lens defined by their specified semi-chord radial distances from the center of the lens to the edge of the lens and their sagittal depth from a reference plane. Some embodiments employ the corneal topography of each eye to apply algorithms for determining the semi-meridian sagittal depth at each control point to allow for empirical ordering and observational fitting of an eye for overnight corneal reshaping. The described embodiments ensure central cornea radius change to correct pre-existing myopia while producing a desired mid-peripheral add power and mid-peripheral add location through the empirical selection of the base curve radius of the lens while also empirically selecting the surface elevation of the lens in each semi-meridian at multiple pre-determined control points on the surface of the lens from the center of the lens to the edge of the lens.

Figure 1:
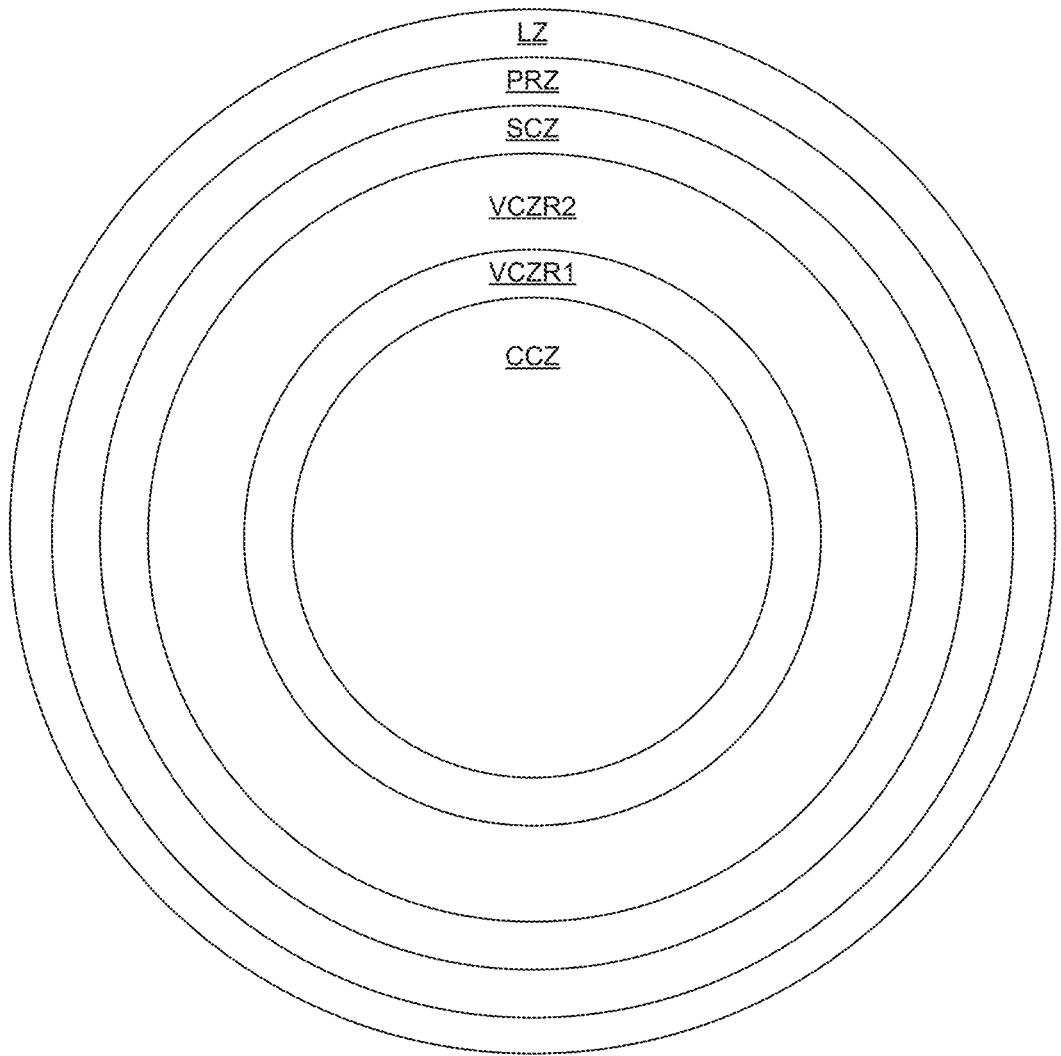
FIG. 1 is a plan view of a posterior surface of a contact lens according to some embodiments of the disclosed technologies.

FIG. 1 is a plan view of a posterior surface of a contact lens according to some embodiments of the disclosed technologies. Referring to FIG. 1, the posterior surface of the contact lens includes multiple annular zones including a central compression zone (CCZ), a first region of a volume control zone (VCZR1), a second region of the volume control zone (VCZR2), a secondary compression zone (SCZ), a peripheral relief zone (PRZ), and a landing zone (LZ). Each of these zones are described in detail below.

Figure 2:
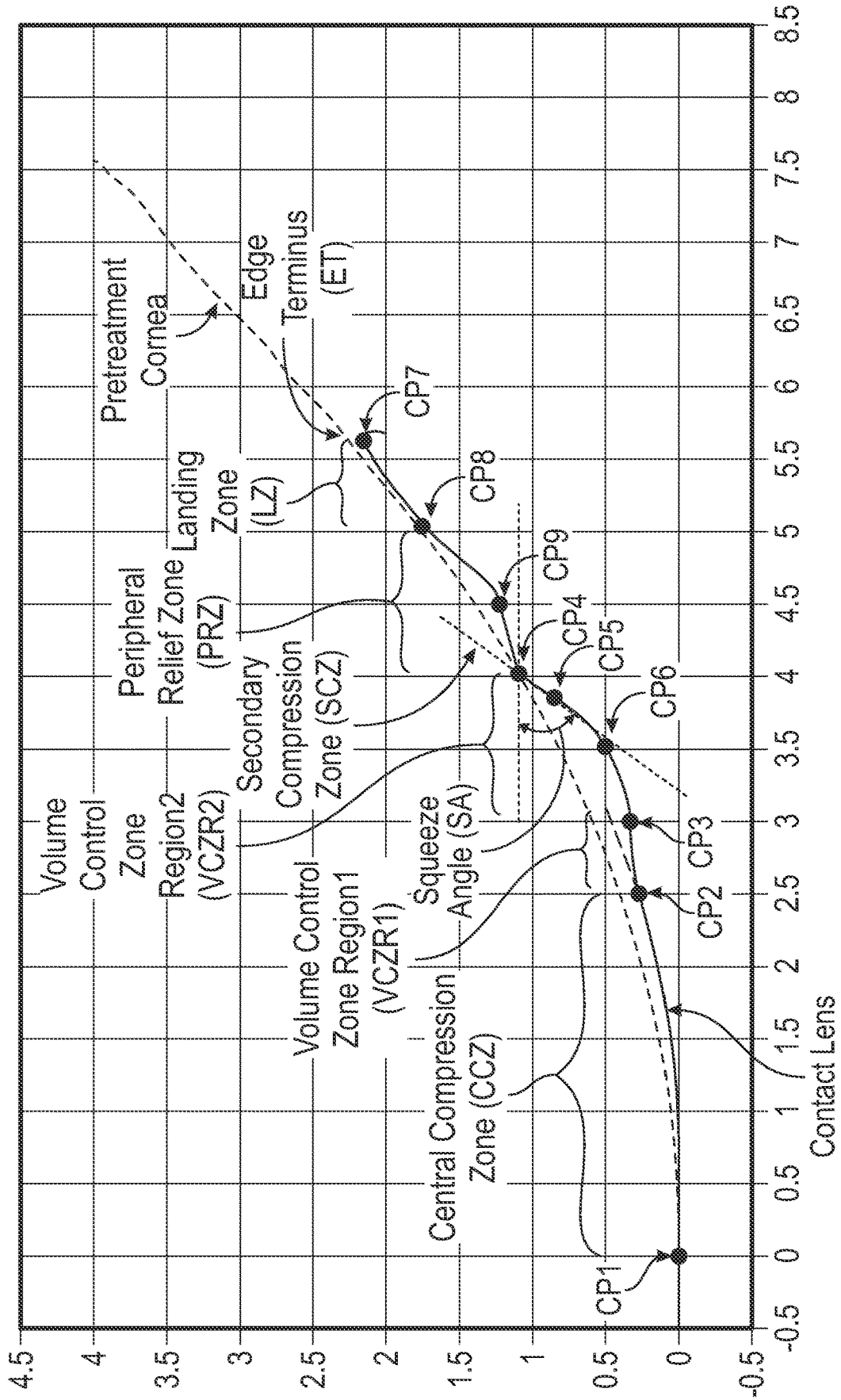
FIG. 2 illustrates a semi-meridian to define a posterior surface of an example contact lens according to some embodiments of the disclosed technology.

FIG. 2 illustrates a semi-meridian to define a posterior surface of an example contact lens according to some embodiments of the disclosed technology. In FIG. 2, the semi-meridian of the contact lens is shown as a continuous solid line having several curves and control points CP. Also shown in FIG. 2 is a pretreatment cornea, shown as a dotted line. The contact lens, and the pretreatment cornea, are plotted on a grid graduated in millimeters. However, FIG. 2 is not drawn to scale. It should be understood that the particular values for the control points CP shown are presented by way of example only, and that other semi-meridians of the contact lens, and semi-meridians of other contact lenses, may have different values for the control points CP. Were the eye rotationally symmetric, the contact lens could be fabricated using only the control points of a single semi-meridian. But as eyes are not rotationally symmetric, the control points of multiple semi-meridians having different surface elevation dimensions may be used to fabricate a single contact lens.

Referring to FIG. 2, the center of the pretreatment cornea, and the center of the contact lens, are located at the origin of the grid. In FIG. 2, the front of the pretreatment cornea, and the anterior surface of the contact lens (not shown) face downward, toward the bottom of the grid. The anterior surface, as practiced by those skilled in the art of contact lens design and manufacturing, may have a predetermined radius in a central optic zone for the purpose of creating a predetermined lens power in conjunction with the posterior surface radius in the central zone. The anterior optic zone surface may be spherical, aspherical, a single radius, or multiple radii designed to produce a multifocal optical power. The peripheral portion of the anterior surface may be designed to create a constant thickness from the posterior surface or may be designed to have varying thicknesses from each corresponding posterior surface control point. The contact lens includes nine control points CP1-CP9, which are related to the zones of the contact lens. However, in other embodiments, different numbers of control points may be employed.

The central compression zone (CCZ) contacts the pretreatment cornea at its center, and extends from a control point CP1 at the center of the semi-meridian to a control point CP2, which in this example is located at a semi-chord radial distance of approximately 2.5 mm.

Peripheral to the central compression zone is the volume control zone, which extends to control point CP4, which in this example is located at a semi-chord radial distance of approximately 4 mm. The volume control zone in this example includes two regions. The first region of the volume control zone (VCZR1) extends to control point CP3, which in this example is located at a semi-chord radial distance of approximately 3 mm. Peripheral to the first region of the volume control zone is the second region of the volume control zone (VCZR2), which includes control points CP6 and CP5, and extends to control point CP4. In this example, control points CP6 and CP5 are located at semi-chord radial distances of approximately 3.4 mm and 3.8 mm, respectively.

Peripheral to the second region of the volume control zone is the secondary compression zone (SCZ), where the contact lens again contacts the pretreatment cornea. Peripheral to the secondary compression zone is the peripheral relief zone (PRZ), which includes a control point CP9 and extends to control point CP8, which in this example is located at a semi-chord radial distance of approximately 5 mm. In this example, control point CP9 is located at a semi-chord radial distance of approximately 4.5 mm.

Peripheral to the peripheral relief zone is the landing zone (LZ), where the contact lens again contacts the pretreatment cornea. The landing zone extends to control point CP7, which in this example is located at a semi-chord radial distance of approximately 5.4 mm. The peripheral end of the landing zone marks the edge terminus (ET) of the contact lens.

A spherical or aspherical base curve may be employed in the central compression zone. The volume control zone, the secondary compression zone, the peripheral relief zone, and the landing zone may be configured using circumferentially varied spline mathematics or other geometry to achieve a desired sagittal depth difference at defined control points along each semi-meridian. The elevation difference may be driven by topographic measurement of the pretreatment cornea at each respective control point and in each semi-meridian of the cornea to be treated. The elevation difference between the points on the posterior lens surface and the respective points on a pre-treatment corneal surface may utilize an axial distance from the lens surface to the corneal surface or a radial distance from the lens surface to the cornea surface. The axial distance forms a line parallel to the axis of the lens while the radial distance is in the direction from the lens surface to a center of rotation of the corneal surface of the respective eye. In a preferred embodiment, the axial distance from the lens surface to the pretreatment corneal surface is used to calculate the elevation difference of the control points on the posterior lens surface and the respective points on the corneal surface. The lens edge may be reconciled to produce a lens that is planar and round, planar and not round, or non-planar and round.

The disclosed contact lens demonstrates improved centration, optimized reduction in refractive myopia of the treated eye, and a pre-determined post-treatment mid-peripheral corneal add power and location. The volume control zone along with the semi-chord radial distance location and angle formed by the secondary compression zone generates the forces to produce the mid-peripheral add power and location. The peripheral relief zone allows the secondary compression zone to impinge and redistribute the corneal epithelium inward to the volume control zone. The uniformly aligned landing zone provides the compression force that produces the central compression and the compression within the secondary compression zone. The rotational asymmetry in the elevation of the landing zone that matches the elevation difference of the pretreatment cornea in two or more semi-meridians provides optimized compression force, lens stability, and improved lens centration. An edge terminus is added to the landing zone. The shape of the posterior contact lens surface is continuous and seamless to avoid any junction induced trauma. In one embodiment, a cubic spline may be employed with knots placed at corresponding control points and controls placed to create the smooth, continuous and seamless surface along with the pre-determined areas under each semi-meridian in the volume control zones and the predetermined angle inward from the secondary compression zone.

The contact lens is seamless because each zone commences at the local slope of the ending of the zone central to it. The knots of the spline of the volume control zone controls the relative sagittal depth of the lens at defined control points along the posterior surface of the semi-meridians of the lens outside of the central compression zone while the controls of the spline provide for the shape of the surface. The most central aspect of the spline is defined by the elevation and local slope at the chord of the optic zone junction and the most peripheral aspect is defined by the desired elevation at each next peripheral control point in each semi-meridian. The local slope of the most peripheral aspect of the volume control zone is defined by the predetermined squeeze angle with its apex at the deepest point of the secondary compression zone. The most peripheral aspect of the secondary compression zone is defined by the local slope of the most central aspect of the peripheral relief zone; and the most peripheral aspect of the peripheral relief zone is defined by the most central aspect of the landing zone. The edge terminus commences at the elevation of the most peripheral aspect of the landing zone.

In some applications, the lenses may be custom-designed for each eye. In other applications, a fitting set may be made from which lenses may be selected. An example fitting set or kit may have one overall diameter (OAD; e.g., in the range of 10.5 mm to 11.5 mm), up to five base curve radii increments (BCRI), each with a single optic zone diameter and one volume control zone width with up to five volume control zone areas for each, three secondary compression zone depths for each, one peripheral relief zone, and one landing zone. This fitting set would have 75 lenses (1 OAD×5 BCRI×5 VCZ areas×3 SCZ depths). A lookup table or computer application may be produced to suggest the first fitting set lens by entry of the manifest refraction and the central keratometry or corneal topography gathered by standard clinical testing.

A preferred empirical method without a fitting set and in the absence of corneal topography is to empirically design a first observation lens to be manufactured by use of the manifest refraction and standard keratometry to predict the base curve radius; the amount of treatment in diopters and mean biometric data to predict the first and second regions of the volume control zone; the amount of treatment and mean biometric data to predict the secondary compression zone depth; standard peripheral relief zone height; and mean biometric data to predict the local slope and sagittal depth of the central portion of the landing zone. This first lens designed empirically from clinical data may serve as a lens for observation for ordering a second lens. Note that the empirically designed first observation lens is expected to include rotational asymmetry that is based on biometric mean data that reveal the asymmetry.

Figure 3:
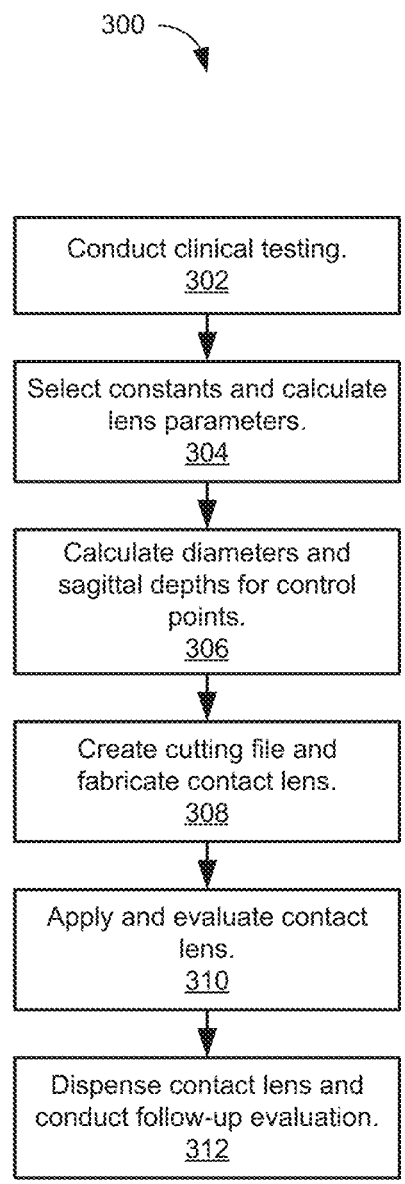
FIG. 3 is a flowchart illustrating an overview process for producing a contact lens for corneal reshaping according to some embodiments of the disclosed technologies.

FIG. 3 is a flowchart illustrating an overview process 300 for producing a contact lens for corneal reshaping according to some embodiments of the disclosed technologies. The elements of the process 300 are presented in one arrangement. However, it should be understood that one or more elements of the process may be performed in a different order, in parallel, omitted entirely, and the like. Furthermore, the process 300 may include other elements in addition to those presented.

Referring to FIG. 3, the process 300 may include conducting clinical testing of the eye, at 302. The clinical testing may include determination of unaided visual acuity, refraction, binocular vision, peripheral refraction, eye health, keratometry, corneal diameter, corneal topography, lid position and aperture size, pupillometry, and the like.

The process 300 may include selecting constants and calculating lens parameters, at 304. These may include base curve radius, optic zone diameter, overall diameter, mid-peripheral add power, the semi-chord radial distance of the center of the mid-peripheral add power, lens power, and the like.

The process 300 may include calculating diameters and sagittal depths for control points of the posterior surface of the contact lens, at 306. These calculations may be based on biometric mean data, measured corneal topography, or the like, or combinations thereof. These calculations are described in detail below. Following these calculations, control points for the anterior surface may be calculated, for example using thickness rules or constants from one or more of the posterior surface control points to one or more of the anterior surface control points and incorporating the required anterior central radius or radii of curvature to produce the desired lens power or powers in the event of multifocal optics, or the like.

The process 300 may include creating a cutting file and fabricating a contact lens, at 308. For example, a semi-meridian for the posterior surface of the contact lens may be calculated using the control points, for example as shown in FIG. 1. The semi-meridian surface may be generated using splines, geometric segments, or the like, or combinations thereof. The contact lens may be fabricated with usual and customary good manufacturing practices from standard extended wear rigid gas permeable material, or the like. For example, a polish-free computer numerically controlled lathe may be employed to cut the contact lens. Cutting may be followed by a contour inspection of the posterior surface of the contact lens to determine the finished posterior surface matches the intended shape.

The process 300 may include applying and evaluating the contact lenses, at 310. This may include capturing an image of the contact lens on the eye of the patient. The image may be analyzed to assess the lens-eye relationship and to measure lens centration. The evaluation may include steps to determine the over-refraction, to measure visual acuity, and the like. The process 300 may conclude with dispensing the contact lens, and conducting one or more follow-up evaluations, at 312.

Figure 4A:
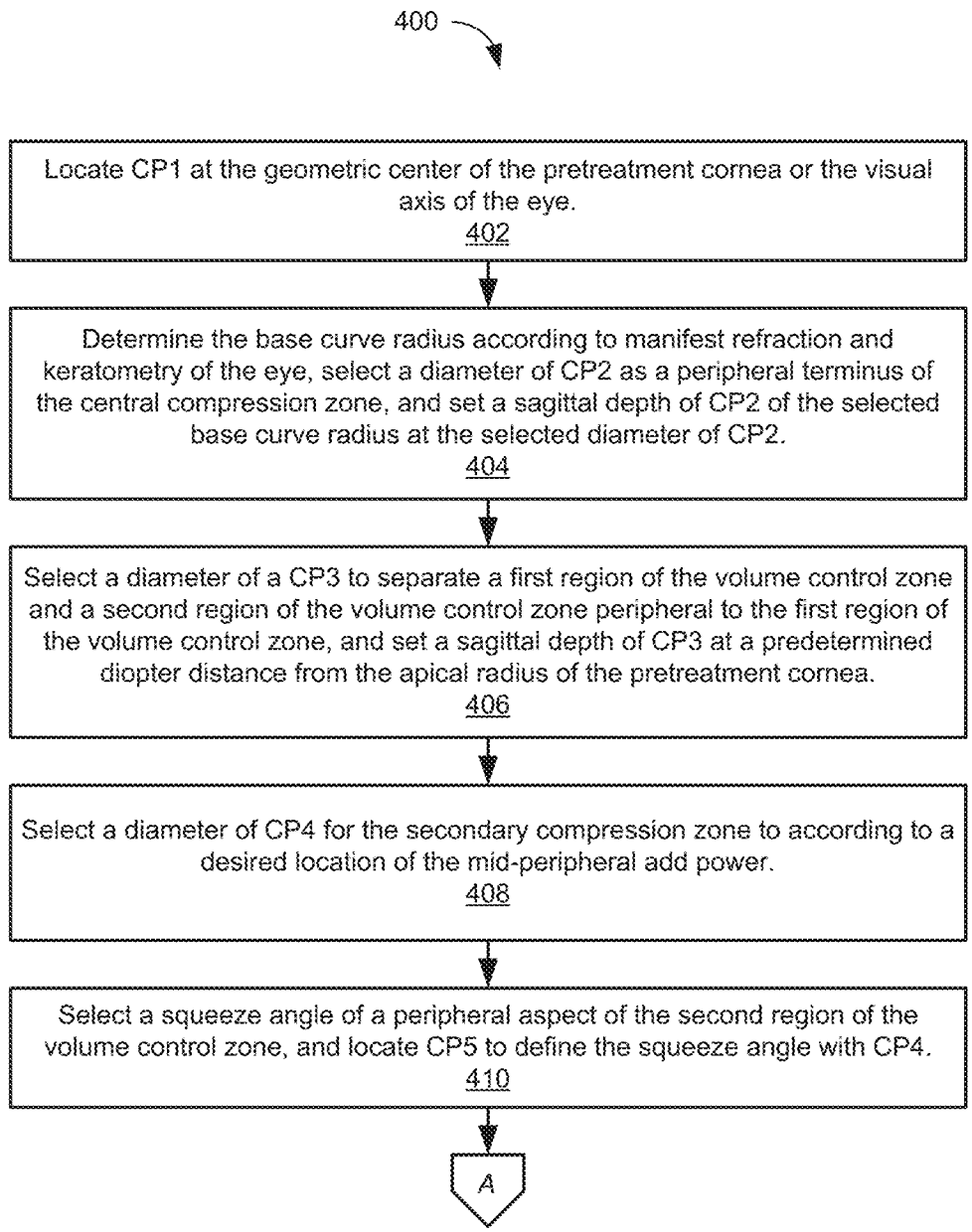
FIGS. 4A and 4B are a flowchart illustrating an overview process for defining a contact lens for corneal reshaping according to some embodiments of the disclosed technologies.
Figure 4B:
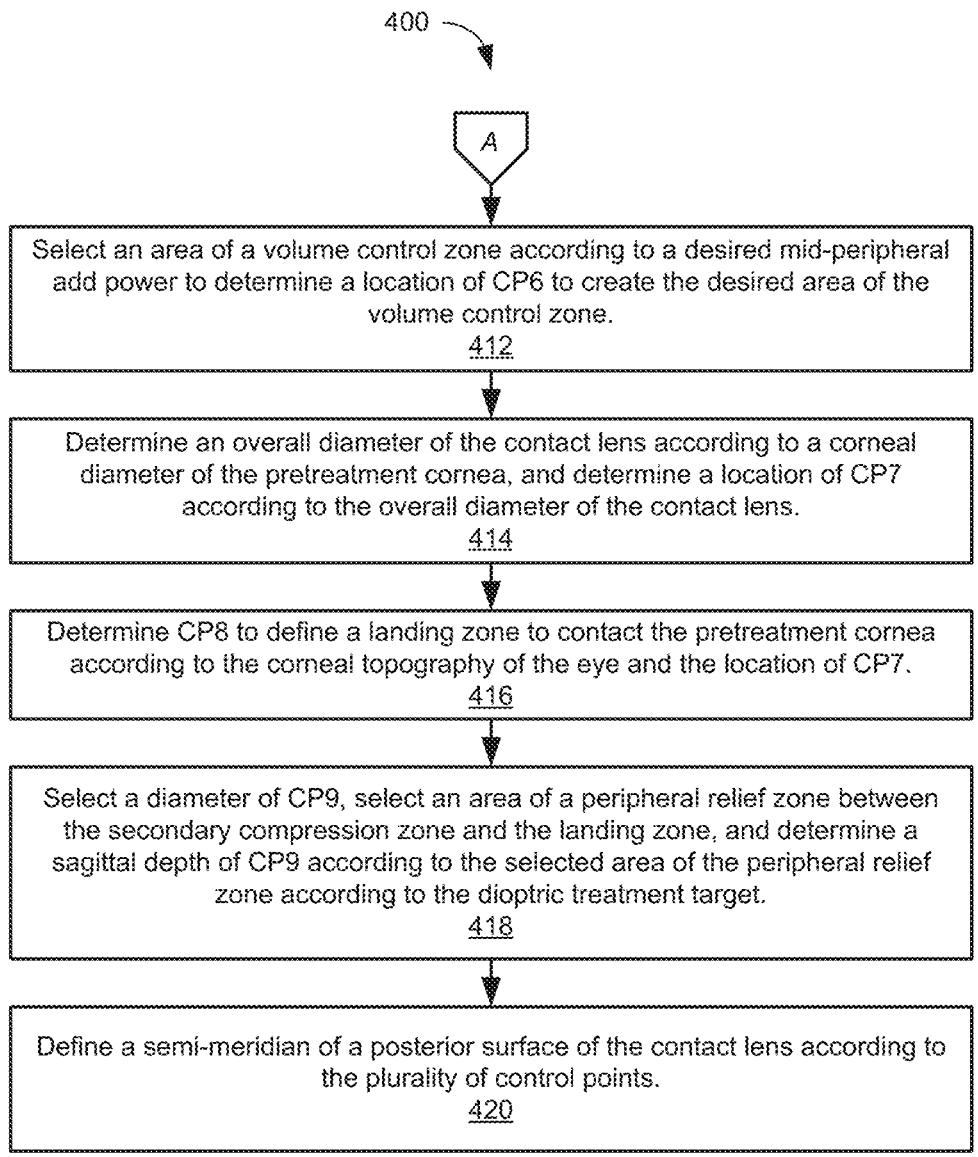

FIGS. 4A and 4B are a flowchart illustrating an overview process 400 for defining a contact lens for corneal reshaping according to some embodiments of the disclosed technologies. The elements of the process 400 are presented in one arrangement. However, it should be understood that one or more elements of the process may be performed in a different order, in parallel, omitted entirely, and the like. Furthermore, the process 400 may include other elements in addition to those presented.

Referring to FIG. 4A, the process 400 may include locating a control point CP1 at the geometric center of the lens to correspond with the geometric center of the pretreatment cornea, at 402. The process 400 may include determining the base curve radius according to manifest refraction and keratometry of the eye to be treated, selecting a diameter of a control point CP2 as a peripheral terminus of the central compression zone CCZ, and setting a sagittal depth of control point CP2 at the sagittal depth of the selected base curve radius at the selected diameter of control point CP2, at 404.

The process 400 may include selecting a diameter of control point CP3 to separate a first region of the volume control zone and a second region of the volume control zone peripheral to the first region of the volume control zone, and set a sagittal depth of control point CP3 at a predetermined diopter distance from the apical radius of the pretreatment cornea, at 406. In one embodiment, the sagittal depth difference of CP3 from the cornea is intended to be a constant and independent of the amount of targeted treatment. In this embodiment, all treatment lenses will have the same sagittal depth difference from the underlying cornea at CP3 regardless of the differences in the targeted treatment or the difference between the central corneal radius and the radius of the base curve of the treatment lens. The second region of the volume control zone is used to accommodate eyes having different mid-peripheral elevation differences, to equalize the area under each semi-meridian, to control the location of the increased corneal power produced under this zone, and to improve the centration of the lens. The circumferential equalization of area under each semi-meridian eliminates the fitting of toric or dual elevation by allowing a non-toric base curve and a circumferential elevation difference in the volume control zone to prevent the lens from having heavy bearing on the shallow semi-meridians of the pretreatment cornea and to prevent z-axis tilting and decentration toward the deep semi-meridians of the cornea.

The process 400 may include selecting a diameter or semi-chord radial distance of a control point CP4 for the secondary compression zone to according to a desired location of the mid-peripheral add power, at 408. The sagittal depth of the secondary compression zone SCZ at control point CP4 is a function of the sagittal height of the underlying pretreatment cornea at control point CP4, the apex of the zone. The posterior surface proceeds to the next control point CP9 to determine the height of the peripheral relief zone PRZ. In one embodiment the height of control point CP9 from the underlying pre-treatment cornea is determined by the amount of central treatment in diopters. For example, the height of control point CP9 from the underlying cornea may be equal to 6 microns per diopter of treatment. The peripheral relief zone then descends to a control point CP8. The elevation of control point CP8 corresponds to the measured elevation of the pretreatment cornea at the semi-chord radial distance of the commencement of the landing zone LZ. The semi-chord radial distance of control point CP8 is defined by the semi-chord radial distance of control point CP7 and a minimum desired width between control points CP8 and CP7. In one embodiment the semi-chord radial distance of control point CP7 is defined by the measured horizontal corneal diameter. For example, the lens diameter may be selected to be 90% of the measured corneal diameter and the semi-chord radial distance of control point CP7 is then determined to be 45% of the corneal diameter. The range of the desired semi-chord width from control points CP8 to CP7 is 0.8 to 1.6 mm. The edge terminus ET at control point CP7 is then integrated into the sagittal depth of the lens at the most peripheral aspect of the landing zone LZ. The sagittal depth of control point CP7 is selected as a function of the known ocular contour and a pre-selected edge lift from the underlying cornea at the desired semi-chord radial distance of control point CP7. For example, the desired pre-selected edge lift from the underlying cornea at control point CP7 may be 40 to 80 microns.

The spline for the secondary compression zone SCZ may commence at the local slope of the last control point CP5 in the volume control zone spline and may be calculated to create an angle of incidence of the secondary compression zone SCZ on the underlying pretreatment cornea that optimizes the movement of tissue medially into the volume control zone, referred to herein as the squeeze angle (SA). The process 400 may include selecting a squeeze angle of a peripheral aspect of the second region of the volume control zone, and locating a control point CP5 to define the squeeze angle with control point CP4, at 410. The angle may be measured from a line perpendicular to the axis of the lens that passes through control point CP4 or may be measured from the local slope of the underlying cornea at control point CP4. For example, the local slope of the pre-treatment cornea at control point CP4 may be measured to be 28 degrees and the desired angle between the pre-treatment cornea and the posterior lens surface may be 5 degrees. Thereby, the prescribed angle created by control point CP5 inward from the apex at control point CP4 and from a horizontal line passing through control point CP4 would be reported as 33 degrees from horizontal.

Referring now to FIG. 4B, the process 400 may include selecting an area of the volume control zone according to a desired mid-peripheral add power to determine a location of control point CP6 to create the desired area of the volume control zone, at 412. The area of the volume control zone may be estimated to approximate the area under the posterior surface of a second or third generation corneal reshaping lens with a 3.00 Diopter target treatment when the lens is placed on a pre-treatment cornea. Second and third generation CRT lenses are, as a rule, fit about 1.00 Diopter longer in radius than the target treatment. Therefore, the targeted or desired area of a semi-meridian of the volume control zone may be estimated according to the area under a 4.00 D longer radius of curvature lens on a mean cornea with a mean optic zone diameter and mean reverse curve or return zone width; and a mean reverse curve radius or return zone depth. The targeted or desired total area under a single semi-chord radial distance can include from the center of the lens, control points CP1 to CP4, or the total volume control zone from control points CP2 to CP4, or only the second region of the volume control zone, control points CP3 to CP4. For example, the area from control points CP2 to CP4 for a third or fourth generation CRT lens having an optic zone diameter of 5.0 mm; a reverse curve width of 1.5 mm; and a base curve radius of 4.00 Diopters (approximately 0.8 mm longer than the radius of the pretreatment cornea) is estimated to be $1.58 \times 10^4$ square microns or 0.0158 square millimeters. The desired area in a semi-meridian will vary according to the semi-chord radial distance of control points CP2, CP3 and CP4. Control point CP4 regulates the semi-chord radial distance of the mid-point of the mid-peripheral power addition. The closer to the center of the lens the mid-peripheral add power is desired, the shorter the semi-chord radial distance of control point CP4. The shorter the semi-chord radial distance of control point CP4, the lower the area of the respective volume control zone when control points CP2 and CP3 are held constant. In one embodiment, the semi-chord radial distance of control point CP2 is held equal to or greater than 1.5 mm and control point CP3 is held equal to or greater than 2.2 mm. A decreased semi-meridian radial distance of control point CP4 decreases the semi-meridian radial distance of the mid-point of the post treatment mid-peripheral add power. For a given semi-meridian radial distance of control point CP4, the greater the area within the volume control zone, the higher the mid-peripheral add power. To be clear, the modulation of the semi-meridian radial distance of control point CP4 controls the radial location of the mid-peripheral add power while the area between the posterior lens surface and the pre-treatment cornea within the volume control zone modulates the mid-peripheral add power. The semi-meridian radial distance of control point CP6 modulates the shape of the mid-peripheral add power.

The process 400 may include determining an overall diameter of the contact lens according to a corneal diameter of the pretreatment cornea, and determining a location of a control point CP7 according to the overall diameter of the contact lens, at 414.

The process 400 may include determining a control point CP8 to define the landing zone LZ to contact the pretreatment cornea according to the corneal topography of the eye and the location of control point CP7, at 416. The circumferential elevation features of the secondary compression zone SCZ and landing zone LZ results in a uniform edge lift circumferentially which facilitates improved centration and improved comfort. The semi-meridian sagittal depth control design may use different splines in at least one semi-meridian of at least one zone of the lens outside of the optic zone. The amount of sagittal depth difference can be prescribed around a nominal value which is used for the majority of normal eyes or empirically determined by elevation data from corneal topography.

The process 400 may include selecting a diameter of a control point CP9, selecting an area of a peripheral relief zone between the secondary compression zone and the landing zone, and determining a sagittal depth of control point CP9 according to the selected area of the peripheral relief zone, at 418. In an alternative embodiment, the sagittal depth of control point CP9 is determined as a function of the treatment target for the respective eye. It is known by those skilled in the art that the corneal apex retreats approximately 6 microns per diopter of achieved treatment. Control point CP9 may be placed a distance from the underlying cornea of 6 microns per diopter. For example, when 3.00D of treatment is targeted, control point CP9 may be placed 18 microns from the underlying corneal surface when control points CP1, CP4 and CP8 are placed to contact the corneal surface. Greater clearance is understood to be acceptable while lesser clearance may impede treatment or require the entire lens surface from control points CP4 to CP7 to compress the cornea.

Table 1 below provides an example wherein the semi-meridian corneal elevation at control points at semi-meridian radial distances is provided and the posterior surface sagittal depths are determined according to the methods of one embodiment of the present invention.

TABLE 1

| Description of Control Point | Control Point Number | Example Corneal Elevation mm | Lens Semi Chord (x) mm | Posterior Lens Sag (z) mm | Lens to Cornea Clearance (microns) |
|---|---|---|---|---|---|
| Corneal Apex | 1 | 0.000 | 0.00 | 0.000 | 0 |
| Outer boundary or junction of optic zone | 2 | 0.343 | 2.30 | 0.313 | 30 |
| Volume control zone region one outer junction | 3 | 0.403 | 2.50 | 0.371 | 32 |
| Voume control zone area control point | 6 | 0.523 | 2.80 | 0.487 | 36 |
| Volume control zone inward facing angle control point | 5 | 0.646 | 3.10 | 0.628 | 18 |
| Secondary compression zone maximum contact point | 4 | 0.732 | 3.30 | 0.732 | 0 |
| Peripheral relief zone area control point | 9 | 1.005 | 3.85 | 0.987 | 18 |
| Landing zone first contact point | 8 | 1.339 | 4.40 | 1.339 | 0 |
| Edge terminus control point | 7 | 2.073 | 5.40 | 2.013 | 60 |

Clinical measurements and design inputs:
1. Treatment target = −3.00 Diopters
2. Flat keratometry = 7.80 mm
3. Base Curve radius = 8.60 mm
3. Corneal diameter = 11.9 mm
4. Radial semi-chord distance of mid-peripheral add power = 2.8 mm The process 400 may include defining the semi-chord radial distances and sagittal depths of a semi-meridian of a posterior surface of the contact lens according to control points CP1-CP9, at 420. Following definition of one or more semi-meridians, the contact lens may be fabricated, for example as described above. These control point semi-meridian radial distances and corresponding depths are the inputs for a computer program product that completes the required x, y, and z points for the full lens surface.

The disclosed technologies may be applied to the corneal reshaping portion of corneal rigid lenses as well as the corneal reshaping portion of lenses having a diameter greater than the cornea, for example including scleral contact lenses, hybrid contact lenses and soft contact lenses. The edge terminus is not connected to the anterior surface at control point CP7 for embodiments where the lens has a diameter greater than the cornea. Rather, the terminus of the peripheral landing zone is connected to a next peripheral zone on the posterior surface that extends beyond the diameter of the cornea in at least one semi-meridian.

Figure 5:
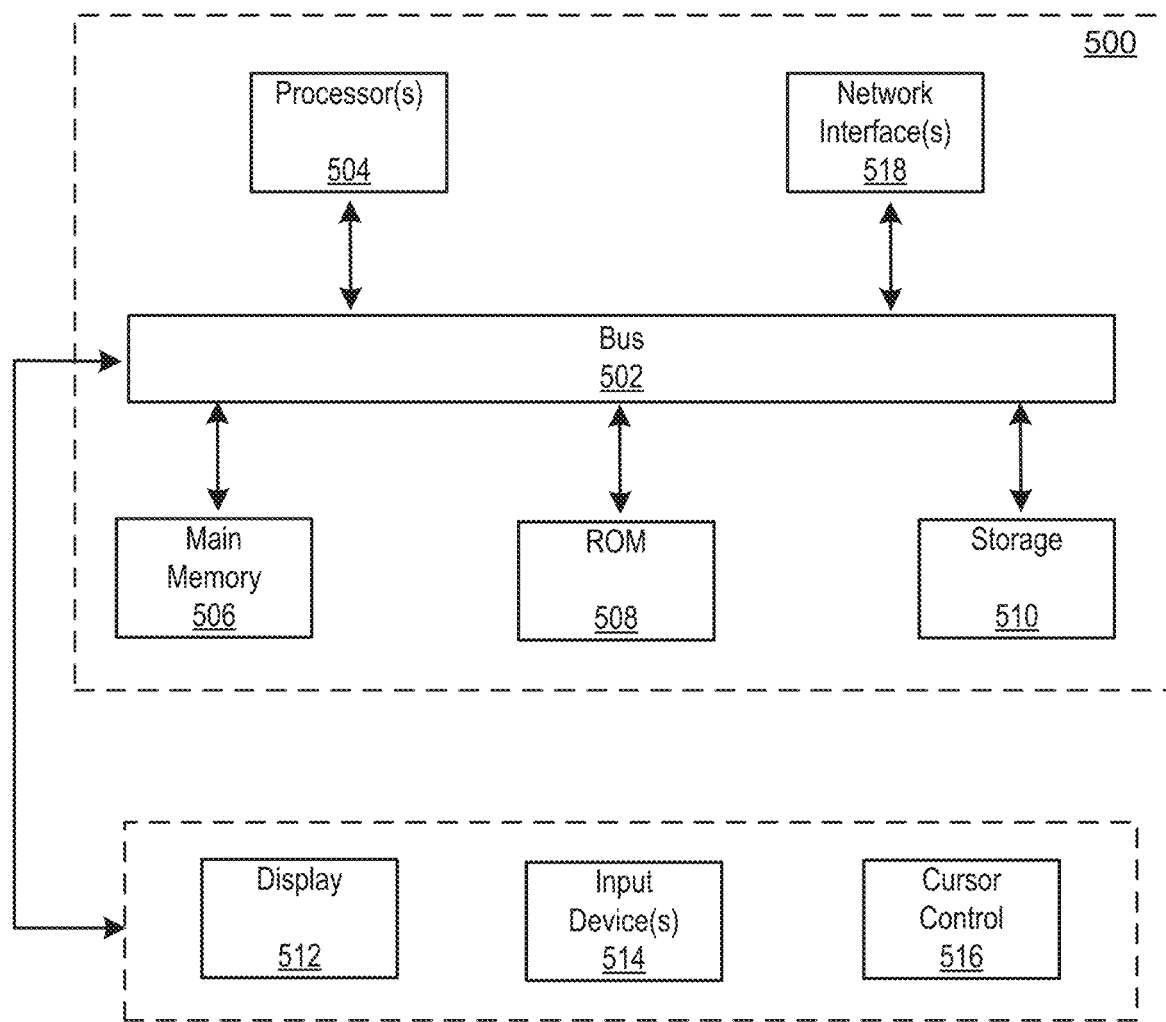
FIG. 5 depicts a block diagram of an example computer system in which embodiments described herein may be implemented.

FIG. 5 depicts a block diagram of an example computer system 500 in which embodiments described herein may be implemented. The computer system 500 includes a bus 502 or other communication mechanism for communicating information, one or more hardware processors 504 coupled with bus 502 for processing information. Hardware processor(s) 504 may be, for example, one or more general purpose microprocessors.

The computer system 500 also includes a main memory 506, such as a random access memory (RAM), cache and/or other dynamic storage devices, coupled to bus 502 for storing information and instructions to be executed by processor 504. Main memory 506 also may be used for storing temporary variables or other intermediate information during execution of instructions to be executed by processor 504. Such instructions, when stored in storage media accessible to processor 504, render computer system 500 into a special-purpose machine that is customized to perform the operations specified in the instructions.

The computer system 500 further includes a read only memory (ROM) 508 or other static storage device coupled to bus 502 for storing static information and instructions for processor 504. A storage device 510, such as a magnetic disk, optical disk, or USB thumb drive (Flash drive), etc., is provided and coupled to bus 502 for storing information and instructions.

The computer system 500 may be coupled via bus 502 to a display 512, such as a liquid crystal display (LCD) (or touch screen), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. In some embodiments, the same direction information and command selections as cursor control may be implemented via receiving touches on a touch screen without a cursor.

The computing system 500 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 500 may implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor(s) 504 executing one or more sequences of one or more instructions contained in main memory 506. Such instructions may be read into main memory 506 from another storage medium, such as storage device 510. Execution of the sequences of instructions contained in main memory 506 causes processor(s) 504 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 510. Volatile media includes dynamic memory, such as main memory 506. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 502. Transmission media can also take the form of acoustic or light waves, such as those generated during radio-wave and infra-red data communications.

The computer system 500 also includes a communication interface 518 coupled to bus 502. Network interface 518 provides a two-way data communication coupling to one or more network links that are connected to one or more local networks. For example, communication interface 518 may be an integrated services digital network (ISDN) card, cable modem, satellite modem, or a modem to provide a data communication connection to a corresponding type of telephone line. As another example, network interface 518 may be a local area network (LAN) card to provide a data communication connection to a compatible LAN (or a WAN component to communicate with a WAN). Wireless links may also be implemented. In any such implementation, network interface 518 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 518, which carry the digital data to and from computer system 500, are example forms of transmission media.

The computer system 500 can send messages and receive data, including program code, through the network(s), network link and communication interface 518. In the Internet example, a server might transmit a requested code for an application program through the Internet, the ISP, the local network and the communication interface 518.

The received code may be executed by processor 504 as it is received, and/or stored in storage device 510, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 500.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A contact lens for reshaping a pretreatment cornea of an eye of a patient, comprising:
an anterior surface; and
a posterior surface having a semi-meridian defining:
a central compression zone to contact the pretreatment cornea,
a volume control zone peripheral to the central compression zone, wherein:
the volume control zone is defined by at least first CP3 and second CP4 geometric control points connected by at least one of a spline, a polynomial, a conic section, or an uncurved segment,
the second geometric control point CP4 is to contact the pretreatment cornea and is peripheral to the first geometric control point CP3, and
the first geometric control point CP3 is positioned to define a predetermined angle between (i) a line connecting the first CP3 and second CP4 control points and (ii) a horizontal line through the second control point CP4,
a secondary compression zone to contact the pretreatment cornea, wherein the secondary compression zone is peripheral to the volume control zone,
a peripheral relief zone peripheral to the secondary compression zone,
a landing zone to contact the pretreatment cornea, wherein the landing zone is peripheral to the peripheral relief zone, and
an edge terminus peripheral to the landing zone.

2. The contact lens of claim 1, wherein a radius of the central compression zone is spherical.

3. The contact lens of claim 1, wherein a radius of the central compression zone is aspherical.

4. The contact lens of claim 1, wherein a diameter of the central compression zone is between 3.0 and 7.0 mm.

5. The contact lens of claim 1, wherein:
a semi-chord radial distance of the first geometric control point CP4 is in a range of 2.6 mm to 5.2 mm.

6. The contact lens of claim 1, wherein:
the secondary compression zone has a width in a range of 0.2 mm to 0.8 mm.

7. The contact lens of claim 1, wherein:
the secondary compression zone is defined by a shape having at least one control point within the secondary compression zone, the shape defined by one of:
a spline;
a polynomial;
a convex conic section; or
an uncurved segment.

8. The contact lens of claim 1, wherein:
the peripheral relief zone is defined by at least one control point positioned to have a z-axis separation from the pretreatment cornea that is at least 6 microns per diopter of attempted reduction of central refractive error.

9. The contact lens of claim 1, wherein:
the peripheral relief zone has a width of between 0.4 mm and 1.2 mm.

10. The contact lens of claim 1, wherein:
the peripheral landing zone is defined by a shape having at least one control point within the peripheral landing zone, the shape defined by one of:
a spline;
a polynomial;
a conic section;
an angled curved section; or
an angled uncurved section.

11. The contact lens of claim 1, wherein:
an edge terminus of the posterior surface commences at the most radially peripheral aspect of the peripheral landing zone and connects to the most peripheral aspect of the anterior surface; and
the edge terminus of the posterior surface is defined by:
an ellipse,
a conic section, or
a spline.

12. The contact lens of claim 1, wherein:
the volume control zone and the secondary compression zone are defined by a single spline.

13. A contact lens for reshaping a pretreatment cornea of an eye of a patient, comprising:
an anterior surface; and
a posterior surface having a semi-meridian defining:
a central compression zone to contact the pretreatment cornea,
a volume control zone peripheral to the central compression zone, wherein:
the volume control zone is defined by at least first CP3 and second CP4 geometric control points connected by at least one of a spline, a polynomial, a conic section, or an uncurved segment,
the second geometric control point CP4 is to contact the pretreatment cornea and is peripheral to the first geometric control point CP3, and
the first geometric control point CP3 is positioned to define a predetermined angle between (i) a line connecting the first CP3 and second CP4 control points and (ii) a line that represents a local slope of the pretreatment cornea through the second control point CP4,
a secondary compression zone to contact the pretreatment cornea, wherein the secondary compression zone is peripheral to the volume control zone,
a peripheral relief zone peripheral to the secondary compression zone,
a landing zone to contact the pretreatment cornea, wherein the landing zone is peripheral to the peripheral relief zone, and
an edge terminus peripheral to the landing zone.

14. The contact lens of claim 13, wherein a radius of the central compression zone is spherical.

15. The contact lens of claim 13, wherein a radius of the central compression zone is aspherical.

16. The contact lens of claim 13, wherein a diameter of the central compression zone is between 3.0 and 7.0 mm.

17. The contact lens of claim 13, wherein:
a semi-chord radial distance of the first geometric control point CP4 is in a range of 2.6 mm to 5.2 mm.

18. The contact lens of claim 13, wherein:
the secondary compression zone has a width in a range of 0.2 mm to 0.8 mm.

19. The contact lens of claim 13, wherein:
the secondary compression zone is defined by a shape having at least one control point within the secondary compression zone, the shape defined by one of:
a spline;
a polynomial;
a convex conic section; or
an uncurved segment.

20. The contact lens of claim 13, wherein:
the peripheral relief zone is defined by at least one control point positioned to have a z-axis separation from the pretreatment cornea that is at least 6 microns per diopter of attempted reduction of central refractive error.

21. The contact lens of claim 13, wherein:
the peripheral relief zone has a width of between 0.4 mm and 1.2 mm.

22. The contact lens of claim 13, wherein:
the peripheral landing zone is defined by a shape having at least one control point within the peripheral landing zone, the shape defined by one of:
a spline;
a polynomial;
a conic section;
an angled curved section; or
an angled uncurved section.

23. The contact lens of claim 13, wherein:
an edge terminus of the posterior surface commences at the most radially peripheral aspect of the peripheral landing zone and connects to the most peripheral aspect of the anterior surface; and
the edge terminus of the posterior surface is defined by:
an ellipse,
a conic section, or
a spline.

24. The contact lens of claim 13, wherein:
the volume control zone and the secondary compression zone are defined by a single spline.

\* \* \* \* \*

UNITED STATES PATENT AND TRADEMARK OFFICE
CERTIFICATE OF CORRECTION

| | | |
|---|---|---|
| PATENT NO. | : 11,953,761 B2 | |
| APPLICATION NO. | : 18/110037 | |
| DATED | : April 9, 2024 | |
| INVENTOR(S) | : Jerome A. Legerton, Jidong Liu and Gaozhi Liu | |

It is certified that error appears in the above-identified patent and that said Letters Patent is hereby corrected as shown below:

On the Title Page

Item (63) Related U.S. Application Data:
"Continuation of application No. 17/616,154, filed as application No. PCT/CN2021/078909 on Mar. 3, 2021, now Pat. No. 11,774,779",
Should read:
-- Continuation of application No. 17/616,154, filed on Dec. 2, 2021, now Pat. No. 11,774,779, a 371 of application No. PCT/CN2021/078909 filed on Mar. 3, 2021 --

Signed and Sealed this
Eleventh Day of June, 2024

Katherine Kelly Vidal
*Director of the United States Patent and Trademark Office*